(12) United States Patent
Nishina et al.

(10) Patent No.: US 12,138,329 B2
(45) Date of Patent: Nov. 12, 2024

(54) GEL CLEANSING AGENT

(71) Applicant: SHISEIDO HONEYCAKE INDUSTRIES CO., LTD., Osaka (JP)

(72) Inventors: Tetsuo Nishina, Osaka (JP); Kouki Harada, Osaka (JP); Yuta Shimizu, Osaka (JP); Uhei Tamura, Osaka (JP)

(73) Assignee: SHISEIDO HONEYCAKE INDUSTRIES CO., LTD., Osaka (JP)

( * ) Notice: Subject to any disclaimer, the term of this patent is extended or adjusted under 35 U.S.C. 154(b) by 381 days.

(21) Appl. No.: 17/602,571

(22) PCT Filed: Dec. 25, 2019

(86) PCT No.: PCT/JP2019/050899
§ 371 (c)(1),
(2) Date: Oct. 8, 2021

(87) PCT Pub. No.: WO2020/230356
PCT Pub. Date: Nov. 19, 2020

(65) Prior Publication Data
US 2022/0175627 A1    Jun. 9, 2022

(30) Foreign Application Priority Data

May 14, 2019  (JP) ................................. 2019-091295

(51) Int. Cl.
| *A61K 8/04* | (2006.01) |
| *A61K 8/39* | (2006.01) |
| *A61K 8/73* | (2006.01) |
| *A61Q 19/10* | (2006.01) |

(52) U.S. Cl.
CPC ................ *A61K 8/042* (2013.01); *A61K 8/39* (2013.01); *A61K 8/73* (2013.01); *A61Q 19/10* (2013.01)

(58) Field of Classification Search
None
See application file for complete search history.

(56) References Cited

FOREIGN PATENT DOCUMENTS

| JP | 5020415 B1 | 9/2012 |
| JP | 2013-100305 A | 5/2013 |
| JP | 6276075 B2 | 2/2018 |
| JP | 2018-39881 A | 3/2018 |
| JP | 6427540 B2 | 11/2018 |
| JP | 6492155 B1 | 3/2019 |

OTHER PUBLICATIONS

International Search Report (ISR) dated Feb. 4, 2020 filed in PCT/JP2019/050899.

*Primary Examiner* — Kyung S Chang
(74) *Attorney, Agent, or Firm* — RANKIN, HILL & CLARK LLP

(57) ABSTRACT

The present invention was made in view of the conventional art, and an object of the present invention is to provide a gel cleansing agent that has a pH of 7.5 or lower and is excellent in foaming property.
The gel cleansing agent comprises:
  2 to 11% by mass of polyoxyethylene alkyl ether carboxylate;
  0.5 to 3% by mass of xyloglucan; and
  0.2 to 3% by mass of a cationized xanthan gum,
and the pH of 1% aqueous solution is 7.5 or lower.

4 Claims, No Drawings

GEL CLEANSING AGENT

RELATED APPLICATION

This application claims the priority of Japanese Patent Application No. 2019-091295 filed on May 14, 2019, which is incorporated herein by reference.

TECHNICAL FIELD

The present invention relates to a gel cleansing agent, and particularly to improvement in a foaming property and a pH characteristic thereof.

BACKGROUND ART

Gel cleansing agents are conventionally known (Patent Literatures 1, 2, and 3), and cleansing components are carried by a gel using xyloglucan (tamarind gum) in any of the above conventional agents. A gel that is formed by xyloglucan is advantageous in that it has a unique elasticity and an excellent feel upon use; however, syneresis easily occurs over time, and browning may occur due to the impact of high pH.

Whereas, a technique of preventing syneresis by using a cationized xanthan gum and preventing browning by decreasing pH has been proposed by the present inventors (Patent Literature 4).

CITATION LIST

Patent Literature

[Patent Literature 1] Japanese Patent No. 5020415 B
[Patent Literature 2] Japanese Patent No. 6427540 B
[Patent Literature 3] Japanese Patent No. 6276075 B
[Patent Literature 4] Japanese Patent No. 6492155 B

SUMMARY OF INVENTION

Technical Problem

Usually, a cleansing agent that uses what is called a fatty acid soap as a cleansing component is relatively excellent in the foaming property; however, the foaming property tends to be slightly poorer in the above-described gel cleansing agents, and the pH is preferably around 7 when mildness to skin is taken into consideration.

However, there was still a room for improvement in these points in the gel cleansing agent described in Patent Literature 4.

The present invention was made in view of the above-described conventional art. An object of the present invention is to provide a gel cleansing agent that has a pH of 7.5 or lower and an excellent foaming property.

Solution to Problem

In order to achieve the above-described object, the gel cleansing agent according to the present invention comprises:
2 to 11% by mass of polyoxyethylene alkyl ether carboxylate;
0.5 to 3% by mass of xyloglucan; and
0.2 to 3% by mass of a cationized xanthan gum,
wherein, the pH of 1% aqueous solution is 7.5 or lower.

In the gel cleansing agent, it is preferred to further comprise 0.01 to 0.5% by mass of a deacylated gellan gum.

In the gel cleansing agent, polyoxyethylene alkyl ether carboxylate is preferably POE (3-5) lauryl ether carboxylate.

In the gel cleansing agent, the neutralization rate of polyoxyethylene alkyl ether carboxylate is preferably 60 to 90%.

Effect of Invention

The gel cleansing agent according to the present invention uses polyoxyethylene alkyl ether carboxylate as the main cleansing agent; therefore, it has a pH of 7.5 or lower, is mild to skin, has a better color tone stability, and can achieve a high foaming property.

DESCRIPTION OF EMBODIMENTS

Preferred embodiments of the present invention are described in the following.

(A) Polyoxyethylene Alkyl Ether Carboxylate

Polyoxyethylene alkyl ether carboxylate formulated, as the main cleansing agent, to the gel cleansing agent of the present invention is a hypoallergenic anionic surfactant, and has the following structure.

R: a saturated alkyl group having 12 to 18 carbon atoms
M: Na, K, amine, 2-amino-2-hydroxymethyl-1,3-propanediol, etc.
n: 0 to 20 on average, preferably 3 to 5 on average In particular, polyoxyethylene lauryl ether carboxylate of which R is a lauryl group is preferred.

Polyoxyethylene alkyl ether carboxylate adopted in the present invention has an excellent solubility and a cleansing property in a region around pH 7, and can exhibit a high foaming property as a gel cleansing agent by xyloglucan.

Ordinary fatty acid salts are required to have the degree of neutralization of around 100%, and when the degree of neutralization is low, inconvenience such as a poor solubility or cleansing property occurs. In particular, when amines (diethanolamine, triethanolamine) are used as a counter ion, it may be necessary to add the counter ion at an amount greater than the theoretical molar amount in order to achieve a suitable degree of neutralization.

Whereas, polyoxyethylene alkyl ether carboxylate can exhibit a sufficient solubility and cleansing ability by adding the counter ion at an amount equal to or less than the theoretical molar amount, and can also achieve an excellent foaming property. According to the studies of the present inventors, necessary functions are exhibited when the counter ion is used at an amount of about 60 to 90% of the theoretical molar amount.

Accordingly, the degree of neutralization of polyoxyethylene alkyl ether carboxylate is 60 to 120%, and preferably 60 to 90% in terms of suppressing the pH.

As a result, the pH of the entire system can be suppressed at a low level (pH 7.5 or lower), and thus browning can be suppressed, stinging irritation can be reduced, and mild sensation to skin can be improved.

Examples of M (counter ion) include: Na; K; organic amine; 2-amino-2-hydroxymethyl-1,3-propanediol;

2-amino-2-methyl-1-propanol; and 2-amino-2-methyl-1,3-propandiol. Even when strong alkaline such as Na and K is used, a cleansing agent of a low pH can be obtained by adjusting the degree of neutralization; however, compounds comprising an amino group such as diethanolamine, triethanolamine, and 2-amino-2-hydroxymethyl-1,3-propanediol are preferred.

The formulation amount of polyoxyethylene alkyl ether carboxylate is preferably 2 to 11% by mass relative to the composition in terms of the cleansing property.

(B) Xyloglucan

Xyloglucan formulated to the gel cleansing agent of the present invention is the main component of seeds of *Tamarindus indica*, a leguminous plant mainly found in the tropics. It is a polysaccharide having a structure expressed with the following formula (I) of which xylose forms α-1,6-glycosidic bond, as a side chain, between a part of the main chain consisting of β-1,4 glucan, and galactose is bonded to a part of xylose. The molecular weight is several hundred thousand.

[Chem. 1]

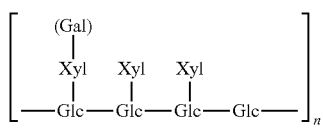

(I)

In the formula: Glc represents glucose; Xyl represents xylose; Gal represents galactose; and n represents a number of bonds.

The formulation amount of xyloglucan (B) is preferably 0.5 to 3% by mass because it becomes a gel state within this range. It is more preferably 1 to 2% by mass. When it is less than 0.5% by mass, it may not be preferred because the cleansing agent may not gel. When it exceeds 3% by mass, it may not be preferred because solubility of the cleansing agent may deteriorate.

To the gel cleansing agent according to the present invention, a commercially available xyloglucan ("GLYLOID 6C", manufactured by Dainippon Pharma Co., Ltd.), for example, can be formulated. When commercially available products are formulated to the gel cleansing agent of the present invention, it is preferred to use one that is purified as much as possible. The molecular weight of xyloglucan to be used is not particularly limited.

To the gel cleansing agent according to the present invention, xyloglucan produced by a known method such as the method described in the product catalogue of the above-described "GLYLOID 6C" can be formulated. That is, xyloglucan can be produced by: removing foreign matters from a tamarind seed; dissolving the tamarind seed in water; removing impurities therefrom to transparentize the solution; drying; and finely crushing.

(C) Cationized Xanthan Gum

The cationized xanthan gum used in the present invention is a water-soluble polymer of which xanthan gum is modified by cationization. Xanthan gum has a structure as shown in the following formula (II).

[Chem. 2]

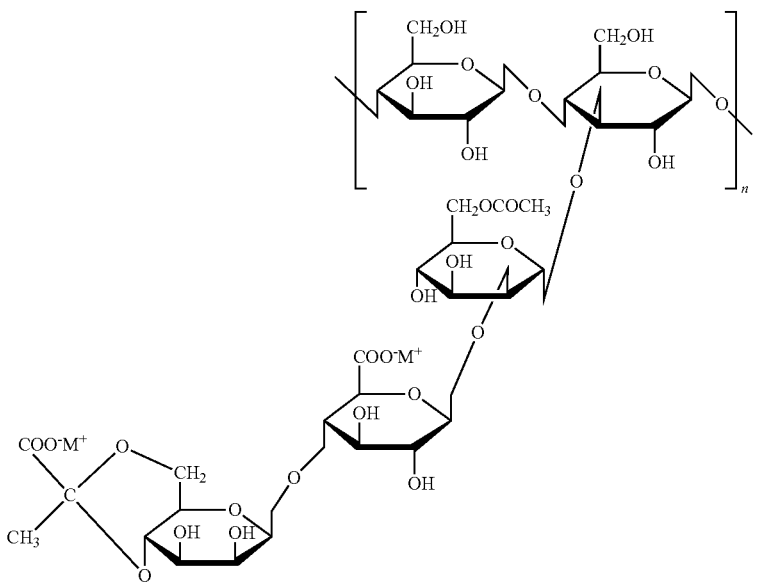

$M^+ = Na^+, K^+, 1/2Cs^{1+}$

By modifying xanthan gum by cationization, the effect of suppressing syneresis of the gel cleansing agent improves; therefore, it is more preferred than using xanthan gum.

The cationization agent for modifying by cationization is one that substitutes a part of a hydroxy group contained in xanthan gum with a cationization group such as a quaternary nitrogen containing group. For example, the cationization agent is preferably 2,3-epoxypropyltrialkyl ammonium salt or 3-chloro-2-hydroxypropyltrialkyl ammonium salt. Examples of these salts include 2,3-epoxypropyltrimethyl ammonium chloride and 3-chloro-2-hydroxypropyltrimethyl ammonium chloride. Examples of other cationization agents include hexamethonium chloride, decamethonium chloride, phenyltrimethyl ammonium chloride, benzyltrimethyl ammonium chloride, tetra-n-butyl ammonium chloride, and tetramethyl ammonium chloride.

The addition amount of the cationization agent can be 0.05 to 1.5 parts by mass relative to 1 parts by mass of xanthan gum, for example.

Xanthan hydroxypropyltrimonium chloride is preferably used as the cationized xanthan gum (C).

The formulation amount of the cationized xanthan gum (C) is preferably 0.2 to 3% by mass because the viscosity of xyloglucan gel may be enhanced and syneresis may be suppressed. It is more preferably 0.3 to 1.5% by mass. When it is less than 0.2% by mass, it may not be preferred because the effect of suppressing syneresis may not be sufficient. When it exceeds 3% by mass, it may not be preferred because solubility of the cleansing agent may deteriorate.

An example of a commercially available product of the cationized xanthan gum (C) may include "Rhaball gum CX" manufactured by DSP GOKYO FOOD & CHEMICAL Co., Ltd.

(D) Deacylated Gellan Gum

A deacylated gellan gum is preferably formulated in the present invention.

The deacylated gellan gum preferably used in the present invention can be obtained by: separating and purifying an extracellular polysaccharide produced by microorganisms (*Sphingomonas elodea*) using glucose as the nutrient source to obtain a gellan gum; and removing the acyl group therefrom.

The deacylated gellan gum has the following structure of which four sugars of two glucose, one glucuronic acid, and one rhamnose are bonded to the main chain.

glucose is added thereto, and dissolved by stirring. Then, the mixture is thickened by adding glycerin, and cooled.

In the gel cleansing agent of the present invention, the pH of 1% aqueous solution is 7.5 or lower, and preferably 6.0 to 7.5 because mild sensation to skin can be achieved.

[Other Components]

Other components can be suitably formulated, within a range of not inhibiting the effects of the present invention, to the gel cleansing agent according to the present invention to produce the gel cleansing agent according to the aimed dosage form. Examples of other components include anionic surfactants, cationic surfactants, amphoteric surfactants, nonionic surfactants, moisturizers, water-soluble polymers, thickeners, film-forming agents, ultraviolet light absorbers, sequestrants, lower alcohols, polyhydric alcohols, oil components, sugars, amino acids, organic amines, polymer emulsions, pH adjusters, skin nutrients, vitamins, antioxidants, antioxidant aids, perfumes, colorants, and water.

Examples of anionic surfactants include: higher alkyl sulfate ester salts (e.g., sodium lauryl sulfate and potassium lauryl sulfate); alkyl ether sulfate ester salts (e.g., POE-lauryl sulfate triethanolamine and sodium POE-lauryl sulfate); N-acyl sarcosinic acids (e.g., sodium lauroyl sarcosinate); higher fatty acid amide sulfonates (e.g., sodium N-myristoyl-N-methyltaurate, sodium methyl cocoyl taurate, and sodium lauroylmethyl taurate); phosphate ester salts (e.g., sodium POE-oleylether phosphate and POE-stearylether phosphate); sulfosuccinates (e.g., sodium di-2-ethylhexyl sulfosuccinate, sodium monolauroyl monoethanolamide polyoxyethylene sulfosuccinate and sodium lauryl polypropylene glycol sulfosuccinate); alkylbenzene sulfonates (e.g. sodium linear dodecylbenzene sulfonate, triethanolamine linear dodecylbenzene sulfonate, and sodium linear dodecylbenzene sulfonate); higher fatty acid ester sulfate ester salts (e.g., sodium hydrogenated glyceryl cocoate sulfate); N-acyl glutamates (e.g., monosodium N-lauroyl glutamate, disodium N-stearoyl glutamate and monosodium N-myristoyl-L-glutamate); acyl glycine salts such as cocoyl glycine salts and lauroyl glycine salts; sulfonated oils (e.g., Turkey red oil); acyl alanine salts such as lauroyl methyl alanine salts; POE-alkyl ether carboxylic acid; POE-alkyl aryl ether carboxylate; α-olefin sulfonate; higher fatty acid ester sulfonate; secondary alcohol sulfate ester salt; higher fatty acid alkylolamide sulfate ester salt;

[Chem. 3]

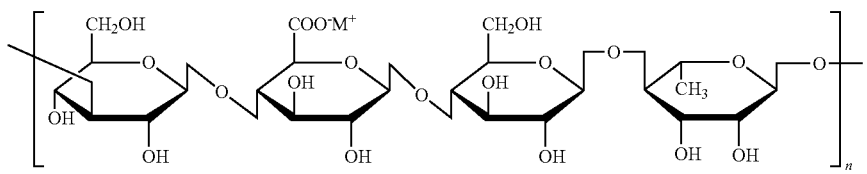

In the present invention, the formulation amount of the deacylated gellan gum is preferably 0.01 to 0.5% by mass, and more preferably 0.05 to 0.1% by mass in the composition.

<Method for Producing the Gel Cleansing Agent>

To produce the gel cleansing agent comprising the above-described components (A) to (C), water and a surfactant such as a soap are put into a production pot, and dissolved by heating. Then, xyloglucan which is wet and dispersed by sodium lauroyl monoethanolamide succinate; N-palmitoyl asparaginate ditriethanolamine; and sodium casein.

Examples of cationic surfactants include: alkyltrimethyl ammonium salts (e.g., stearyltrimethyl ammonium chloride, and behenyltrimethyl ammonium chloride); alkylpyridinium salts (e.g., cetylpyridinium chloride); distearyldimethyl ammonium chloride, dialkyldimethyl ammonium salts; poly (N,N'-dimethyl-3,5-methylenepiperidinium) chloride; alkyl quaternary ammonium salts; alkyldimethylbenzyl ammonium salts; alkylisoquinolinium salts; dialkylmorphonium salts; POE-alkyl amine; alkylamine salts; polyamine fatty acid derivatives; amyl alcohol fatty acid derivatives; benzalkonium chloride; and benzethonium chloride.

Examples of amphoteric surfactants include: imidazoline-based amphoteric surfactants (e.g., sodium 2-undecyl-N,N,N-(hydroxyethylcarboxymethyl)-2-imidazoline, 2-cocoyl-2-imidazolinium hydroxide-1-carboxyethyloxy disodium salt and 2-heptadecyl-N-carboxymethyl-N-hydroxyethyl imidazolinium betaine); betaine-based amphoteric surfactants (e.g., lauryl dimethylaminoacetic acid betaine, alkyl betaine, alkyl amidobetaine, and alkyl sulfobetaine).

Examples of lipophilic nonionic surfactants include sorbitan fatty acid esters (e.g., sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glyceryl polyglyceryl fatty acids (e.g., glyceryl monocotton oil fatty acid, glyceryl monoerucate, glyceryl sesquioleate, glyceryl monostearate, glyceryl α,α'-oleate pyroglutamate, and glyceryl monostearate malate); propylene glycol fatty acid esters (e.g., propylene glycol monostearate); hydrogenated castor oil derivatives; and glyceryl alkyl ether.

Examples of hydrophilic nonionic surfactants include POE-sorbitan fatty acid esters (e.g., POE-sorbitan monooleate, POE-sorbitan monostearate, POE-sorbitan monooleate, POE-sorbitan tetraoleate); POE-sorbit fatty acid esters (e.g., POE-sorbit monolaurate, POE-sorbit monooleate, POE-sorbit pentaoleate, POE-sorbit monostearate), POE-glyceryl fatty acid esters (e.g., POE-monooleate such as POE-glyceryl monostearate, POE-glyceryl monoisostearate, POE-glyceryl triisostearate); POE-fatty acid esters (e.g., POE-distearate, POE-monodioleate, ethyleneglycol distearate); POE-alkyl ethers (e.g., POE-lauryl ether, POE-oleyl ether, POE-stearyl ether, POE-behenyl ether, POE-2-octyldodecyl ether, POE-cholestanol ether); puluronic types (e.g., Puluronic), POE/POP-alkyl ethers (e.g., POE/POP-cetyl ether, POE/POP-2-decyltetradecyl ether, POE/POP-monobutyl ether, POE/POP-hydrogenated lanoline, POE/POP-glycerin ether); tetra POE/tetra POP-ethylenediamine condensation products (e.g., Tetronic); POE-castor oil hydrogenated castor oil derivatives (e.g., POE-castor oil, POE-hydrogenated castor oil, POE-hydrogenated castor oil monoisostearate, POE-hydrogenated castor oil triisostearate, POE-hydrogenated castor oil monopyroglutamate monoisostearate diester, POE-hydrogenated castor oil maleate); POE-beeswax/lanoline derivatives (e.g., POE-sorbitol beeswax); alkanolamide (e.g., coconut oil fatty acid diethanolamide, lauric acid monoethanolamide, fatty acid isopropanolamide, cocamide methyl monoethanol amide); POE-propyleneglycol fatty acid ester; POE-alkyl amines; POE-fatty acid amide; diethylene glycol laurate; sucrose fatty acid ester; alkylethoxydimethylamine oxide; and trioleyl phosphoric acid.

Examples of moisturizers include polyethylene glycol, propylene glycol, dipropylene glycol, glycerin, 1,3-butylene glycol, xylitol, sorbitol, maltitol, chondroitin sulfate, hyaluronic acid, mucoitin sulfate, charonic acid, atelocollagen, cholesteryl-12-hydroxystearate, sodium lactate, bile salt, dl-pyrrolidone carboxylate, alkyleneoxide derivative, short-chain soluble collagen, diglycerin (EO)PO adduct, chestnut rose extract, yarrow extract, and melilot extract.

Examples of natural water-soluble polymers include plant-based polymers (e.g., gum Arabic, gum tragacanth, galactan, guar gum, locust bean gum, gum karaya, carrageenan, pectine, agar, quince seed (*Cydonia oblonga*), algae colloid (brown algae extract), starch (rice, corn, potato, wheat), and glycyrrhizic acid); microorganism-based polymers (e.g., xanthan gum, dextran, succinoglycan, and pullulan), and animal-based polymers (e.g., collagen, casein, albumin, and gelatin).

Examples of semisynthetic water-soluble polymers include starch-based polymers (e.g., carboxymethyl starch and methylhydroxypropyl starch); cellulose-based polymers (e.g., methylcellulose, ethyl cellulose, methylhydroxypropyl cellulose, hydroxyethyl cellulose, cellulose sodium sulfate, hydroxypropyl cellulose, carboxymethyl cellulose, sodium carboxymethyl cellulose, crystalline cellulose, and cellulose powder); and algin acid-based polymers (e.g., sodium alginate and propylene glycol alginate ester).

Examples of synthetic water-soluble polymers include vinyl-based polymers (e.g., polyvinyl alcohol, polyvinyl methyl ether, polyvinylpyrrolidone, and carboxyvinylpolymer); polyoxyethylene-based polymers (e.g., polyoxyethylenepolyoxypropylene copolymer such as polyethylene glycol 20,000, 40,000 and 60,000, and highly polymerized polyethylene glycol); acrylic polymers (e.g., sodium polyacrylate, polyethylacrylate, and polyacrylamide); polyethyleneimine; and cationic polymers.

Examples of thickeners include gum Arabic, carrageenan, gum karaya, gum tragacanth, carob gum, quince seed (*Cydonia oblonga*), casein, dextrin, gelatin, sodium pectate, sodium alginate, methylcellulose, ethyl cellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyldimethylammonium cellulose sulfate, xanthan gum, aluminum magnesium silicate, bentonite, hectorite, aluminum magnesium silicate (veegum), laponite, and silicic anhydride.

Examples of ultraviolet light absorbers include benzoic acid-based ultraviolet light absorbers (e.g., para-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid-based ultraviolet light absorbers (e.g., homomenthyl-N-acetylanthranilate); salicylic acid-based ultraviolet light absorbers (e.g., amyl salicylate, menthyl salicylate, homomenthyl salicylate, octyl salicylate, phenyl salicylate, benzyl salicylate, and p-isopropanolphenyl salicylate); cinnamic acid-based ultraviolet light absorbers (e.g., octyl methoxycinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glyceryl mono-2-ethylhexanoyl-di-paramethoxy cinnamate); benzophenone-based ultraviolet light absorbers (e.g., 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor, 3-benzylidene-d,l-camphor; 2-phenyl-5-methylbenzoxazol; 2,2'-hydroxy-5-methylphenylbenzotriazol; 2-(2'-hydroxy-5'-t-octylphenyl) benzotriazol; 2-(2'-hydroxy-5'-methylphenylbenzotriazol; dibenzalazine;

dianisoylmethane; 4-methoxy-4'-t-butyldibenzoylmethane; 5-(3,3-dimethyl-2-norbomylidene)-3-pentane-2-one, dimorpholinopyridazinone; 2-ethylhexyl-2-cyano-3,3-diphenylacrylate; and 2,4-bis-{[4-(2-ethylhexyloxy)-2-hydroxy]-phenyl}-6-(4-methoxyphenyl)-(1,3,5)-triazine.

Examples of sequestrants include 1-hydroxyethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium hydroxyethyl ethylenediamine triacetate.

Examples of lower alcohols include ethanol, propanol, isopropanol, isobutyl alcohol, and t-butyl alcohol.

Examples of polyhydric alcohols include dihydric alcohols (e.g., ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (e.g., glycerin and trimethylolpropane); tetrahydric alcohols (e.g., pentaerythritol such as 1,2,6-hexanetriol); pentahydric alcohols (e.g., xylitol); hexahydric alcohol (e.g., sorbitol and mannitol); polyhydric alcohol polymers (e.g., diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkyl ethers (e.g., ethylene glycol monomethyl ether, ethylene glycol monoethyl ether, ethylene glycol monobutyl ether, ethylene glycol monomphenyl ether, ethylene glycol monohexyl ether, ethylene glycol mono2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (e.g., diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin monoalkyl ethers (e.g., chimyl alcohol, selachyl alcohol, and batyl alcohol); sugar alcohols (e.g., sorbitol, maltitol, maltotriose, mannitol, sucrose, erythritol, glucose, fructose, starch sugar, maltose, xylitose, and starch sugar hydrogenated alcohol); glycolide; tetrahydrofurfuryl alcohol; POE-tetrahydrofurfuryl alcohol; POP-butyl ether; POP/POE-butyl ether; tripolyoxypropylene glycerin ether; POP-glycerin ether; POP-glycerin ether phosphoric acid; POP/POE-pentaerythritol ether; and polyglycerin.

Examples of monosaccharides include triose (e.g., D-glyceryl aldehyde and dihydroxyacetone); tetrose (e.g., D-erythrose, D-erythrulose, D-threose, and erythritol); pentaose (e.g., L-arabinose, D-xylose, L-lyxose, D-arabinose, D-ribose, D-ribulose, D-xylulose, and L-xylulose); hexalose (e.g., D-glucose, D-talose, D-psicose, D-galactose, D-fructose, L-galactose, L-mannose, and D-tagatose); heptose (e.g., aldoheptose and heplose); octose (e.g., octulose); deoxy sugar (e.g., 2-deoxy-D-ribose, 6-deoxy-L-galactose, and 6-deoxy-L-mannose); amino sugar (e.g., D-glucosamine, D-galactosamine, sialic acid, amino uronic acid, and muramic acid); and uronic acid (e.g., D-grucuronic acid, D-mannuronic acid, L-guluronic acid, D-garacturonic acid, and L-iduronic acid).

Examples of oligosaccharides include sucrose, guntianose, umbelliferose, lactose, planteose, isolignoses, α,α-trehalose, raffinose, lignoses, umbilicin, stachyose, and verbascoses.

Examples of polysaccharides include cellulose, quince seed, chondroitin sulfate, starch, galactan, dermatan sulfate, glycogen, gum arabic, heparan sulfate, hyaluronic acid, gum tragacanth, keratan sulfate, chondoroitin, mucoitin sulfate, guar gum, dextran, kerato sulfate, locust bean gum, succinoglycan, and charonic acid.

Examples of amino acids include neutral amino acids (e.g., threonine and cysteine), and basic amino acids (e.g., hydroxylysine). Examples of amino acid derivatives include sodium acyl sarcosinate (sodium lauroyl sarcosinate), acyl glutamate, sodium acyl β-alanine, glutathione, and pyrrolidone carboxylic acid.

Examples of organic amines include monoethanolamine, diethanolamine, triethanolamine, morpholine, triisopropanolamine, 2-amino-2-methyl-1,3-propandiol, and 2-amino-2-methyl-1-propanol.

Examples of polymer emulsions include acrylic resin emulsions, ethyl polyacrylate emulsions, acryl resin liquids, polyacrylic alkyl ester emulsions, polyvinyl acetate resin emulsions, and natural rubber latex.

Examples of pH adjusters include buffers such as citric acid, lactic acid-sodium lactate, citric acid-sodium citrate, and succinic acid-sodium succinate.

Examples of vitamins include vitamins A, B1, B2, B6, C and E as well as their derivatives, pantothenic acid and its derivatives, and biotin.

Examples of antioxidants include tocopherols, dibutyl hydroxytoluene, butyl hydroxyanisole, and gallic acid esters.

Examples of antioxidant aids include phosphoric acid, citric acid, ascorbic acid, maleic acid, malonic acid, succinic acid, fumaric acid, cephalin, hexametaphosphate, phytic acid, and ethylene diamine tetraacetic acid.

Examples of other components that can be formulated include antiseptics (ethylparaben, butylparaben, chlorphenesin, and phenoxyethanol); antiphlogistic agents (e.g., glycyrrhizic acid derivatives, glycyrrhetinic acid derivatives, salicylic acid derivatives, hinokitiol, zinc oxide, and allantoin); whitening agents (e.g., placenta extract, creeping saxifrage extract, and arbutin); various extracts (e.g., Phellodendri Cortex, goldthread, lithospermum root, Paeonia lactiflora, Swertia japonica, birch, sage, loquat, carrot, aloe, Malva sylvestris, iris, grape, Coix ma-yuen, sponge gourd, lily, saffron, Cnidium officinale, sheng jiang, Hypericum erectum, Onions, garlic, Guinea pepper, Chen pi, Angelica acutiloba, and seaweed), activators (e.g., royal jelly, photosensitive substances, and cholesterol derivatives); blood circulation promoters (e.g., nonyl acid valenyl amide, nicotinic acid benzyl esters, nicotinic acid β-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and γ-orizanol); anti-seborrhea agents (e.g., sulfur and thiantol); anti-inflammatory agents (e.g., tranexamic acid, thiotaurine, and hypotaurine); and oil components (e.g., squalane, jojoba oil, and silicone).

In addition, sequestrants such as disodium edetate, trisodium edetate, sodium citrate, sodium polyphosphate, sodium metaphosphate, gluconic acid, and malic acids; caffeine, tannin, verapamil, tranexamic acid and derivatives thereof, various crude drug extracts such as licorice, Chinese quince, and *Pyrola japonica*; drugs such as tocopherol acetate, glycyrrhetinic acid, glycyrrhizic acid and derivatives thereof, or salts thereof, skin-whitening agents such as vitamin C, magnesium ascorbyl phosphate, ascorbic acid glucoside, arbutin, and kojic acid; amino acids such as arginine and lysine, and derivatives thereof, and saccharides such as fructose, mannose, erythritol, trehalose, and xylitol may further be formulated as necessary.

Preferred embodiments of the present invention are described in the following.

In the following embodiments, evaluation was performed with the following methods.

(1) Foaming Property 400 ml of 2% aqueous solution was stirred with a mixer at a stirring speed of 4300 rpm at 25° C. The liquid volume (ml) after stirring for one minute was evaluated.
  ⊚: 2000 ml or greater
  ◯: 1500 to 2000 ml
  Δ: 1000 to 1500 ml
  X: 1000 ml or lower (2) Appearance The appearance after 24 hours from production at ambient temperature was evaluated.
  ◯: Transparent
  Δ: Semi-transparent
  X: Opaque (3) High-Temperature Stability (Color Tone)

As for the high-temperature stability, the extent of browning was observed after storing for 4 weeks at 60° C.
  ◯: Hardly no browning
  Δ: Slightly browned
  X: Browned (4) Syneresis Rate The gel was cut into a cube of about 2 cm per side, and sealed in a screw tube.

After leaving to stand it in an incubator for one week at a predetermined temperature, the solid gel was taken out from the incubator. The syneresis rate was calculated from its change in weight.

◯: 2% or lower
  ◯Δ: 2 to 5%
  Δ: 5 to 10%
  X: 10% or greater (5) Gel Hardness

After 24 hours from production, the hardness of the gel was measured with a rheometer (8φ) at ambient temperature.

(6) Productivity

In a melted state (80° C.), productivity was measured with a B-type viscometer (No. 3, 12 rpm).
  ⊚: 500 mPa·s or lower
  ◯: 500 to 1000 mPa·s
  Δ: 1000 to 1500 mPa·s
  X: 1500 mPa·s or greater (7) Mild Sensation to Skin Mild sensation to skin was evaluated with lowness of stinging irritation.

That is, assuming that the gel cleansing agent is to be applied directly to a wet face, the test sample was diluted to 50% aqueous solution with an ion-exchanged water.

With a cotton swab to which the test sample was applied, the test sample was applied to an area ranging from an upper cheek to a lower eyelid of a sensory test panelist.

The stinging irritation was evaluated with the highest irritation score which the panelist felt during 8 minutes from immediately after application.

| Irritation score | Criteria of sensory evaluation grade | Grade |
|---|---|---|
| 6 | Unbearable strong sensory irritation is felt | X |
| 5 | Strong sensory irritation is felt | X |
| 4 | Sensory irritation is clearly felt | X |
| 3 | Sensory irritation is felt sometimes | Δ |
| 2 | Some sensory irritation such as itchiness or prickliness is felt | ◯Δ |
| 1 | Some uncomfortable feeling such as coolness, hotness or tightness is felt | ◯ |
| 0 | No sensory irritation is felt CD | ⊚ |

First, upon forming the gel with tamarind gum, the present inventors studied on the effect of suppressing syneresis of a native gellan gum and a deacylated gellan gum.

The results are shown in Tables 1 and 2.

TABLE 1

| | | Test example | | | | | |
|---|---|---|---|---|---|---|---|
| | | 1-1 | 1-2 | 1-3 | 1-4 | 1-5 | 1-6 |
| Moisturizer | Concentrated glycerin | 30 | 30 | 30 | 30 | 30 | 30 |
| Gelling agent | Tamarind seed gum | 1.6 | 1.6 | 1.6 | 1.6 | 1.6 | 1.6 |
| Syneresis suppressing agent | Native gellan gum | — | 0.01 | 0.03 | 0.05 | 0.07 | 0.1 |
| | Deacylated gellan gum | — | — | — | — | — | — |
| Solvent | Ion-exchanged water | to 100 | to 100 | to 100 | to 100 | to 100 | to 100 |
| Evaluation | Appearance (room temp.) | ◯ | X | X | X | X | X |
| | Gel hardness | 46 | 37 | 61 | 113 | 87 | 95 |
| | Syneresis suppressing effect | Δ | Δ | ◯ | ◯ | ◯ | ◯ |

TABLE 2

|  |  | Test example | | | | | |
|---|---|---|---|---|---|---|---|
|  |  | 1-1 | 2-1 | 2-2 | 2-3 | 2-4 | 2-5 |
| Moisturizer | Concentrated glycerin | 30 | 30 | 30 | 30 | 30 | 30 |
| Gelling agent | Tamarind seed gum | 1.6 | 1.6 | 1.6 | 1.6 | 1.6 | 1.6 |
| Syneresis suppressing agent | Native gellan gum | — | — | — | — | — | — |
|  | Deacylated gellan gum | — | 0.01 | 0.03 | 0.05 | 0.07 | 0.1 |
| Solvent | Ion-exchanged water | to 100 | to 100 | to 100 | to 100 | to 100 | to 100 |
| Evaluation | Appearance (room temp.) | ○ | ○ | ○ | ○ | ○ | ○ |
|  | Gel hardness | 46 | 55 | 97 | 90 | 113 | 84 |
|  | Syneresis suppressing effect | Δ | Δ | ○Δ | ○ | ○ | ○ |

As is obvious from Tables 1 and 2, both of the native gellan gum and the deacylated gellan gum exhibited an excellent effect of suppressing syneresis in a concentration-dependent manner.

In particular, with the deacylated gellan gum, the transparency of the formed gel was high, and it was preferable upon obtaining a transparent gel cleansing agent.

Next, the present inventors evaluated on cases when cleansing components were added.

The results are shown in the following Tables 3 to 6.

TABLE 3

|  |  | Test example | | | | |
|---|---|---|---|---|---|---|
|  |  | 3-1 | 3-2 | 3-3 | 3-4 | 3-5 |
| POE alkyl ether carboxylate | Laureth-6 carboxylic acid | 3.29 | 3.29 | 3.29 | 3.29 | — |
| Fatty acid | Lauric acid | — | — | — | — | 0.9 |
|  | Myristic acid | — | — | — | — | 1.5 |
| Neutralizer | Triethanolamine | 0.85 | 0.85 | 0.85 | 0.85 | 3.4 |
| Anionic surfactant | Sodium cocoyl methyl taurate | 2.25 | 2.25 | 2.25 | 2.25 | 2.25 |
| Amphoteric surfactant | Cocamide propyl betaine | 4.47 | 4.47 | 4.47 | 4.47 | 4.47 |
| Gelling agent | Tamarind seed gum | 1.6 | 1.6 | 1.6 | 1.6 | 1.6 |
| Syneresis suppressing agent | Xanthan hydroxypropyl-trimonium chloride | — | — | — | — | — |
|  | Deacylated gellan gum | — | 0.05 | 0.1 | 0.2 | — |
| Moisturizer | Concentrated glycerin | 22 | 22 | 22 | 22 | 22 |
|  | Propanediol | 2 | 2 | 2 | 2 | 2 |
| Chelating agent | EDTA-3Na·2H2O | 0.2 | 0.2 | 0.2 | 0.2 | 0.2 |
| Solvent | Ion-exchanged water | to 100 | to 100 | to 100 | to 100 | to 100 |
| Evaluation | Appearance (room temp.) | ○ | ○ | Δ | X | ○ |
|  | pH (1%) | 7.13 | 6.36 | 6.27 | 6.5 | 8.06 |
|  | Soap (gel hardness) | 63 | 71 | 91 | 106 | 86 |
|  | Syneresis suppressing effect (25° C.) | X | X | X | X | X |
|  | Foaming property | ○ | ○ | ○ | ○ | X |
|  | Productivity (80° C.) | ○ | ◎ | ◎ | ◎ | ◎ |

TABLE 4

|  |  | Test example | | | |
|---|---|---|---|---|---|
|  |  | 4-1 | 4-2 | 4-3 | 4-4 |
| POE alkyl ether carboxylate | Laureth-6 carboxylic acid | 3.29 | 3.29 | 3.29 | 3.29 |
| Neutralizer | Triethanolamine | 0.85 | 0.85 | 0.85 | 0.85 |
| Anionic surfactant | Sodium cocoyl methyl taurate | 2.25 | 2.25 | 2.25 | 2.25 |
| Amphoteric surfactant | Cocamide propyl betaine | 4.47 | 4.47 | 4.47 | 4.47 |
| Gelling agent | Tamarind seed gum | 1.6 | 1.6 | 1.6 | 1.6 |
| Syneresis suppressing agent | Xanthan hydroxypropyl-trimonium chloride | 0.1 | 0.1 | 0.1 | 0.1 |
|  | Deacylated gellan gum | — | 0.05 | 0.1 | 0.2 |
| Moisturizer | Concentrated glycerin | 22 | 22 | 22 | 22 |
|  | Propanediol | 2 | 2 | 2 | 2 |

TABLE 4-continued

|  |  | Test example | | | |
|---|---|---|---|---|---|
|  |  | 4-1 | 4-2 | 4-3 | 4-4 |
| Chelating agent | EDTA-3Na•2H2O | 0.2 | 0.2 | 0.2 | 0.2 |
| Solvent | Ion-exchanged water | to 100 | to 100 | to 100 | to 100 |
| Evaluation | Appearance (room temp.) | ○ | Δ | Δ | X |
|  | pH (1%) | 6.42 | 7.26 | 6.38 | 6.31 |
|  | Soap (gel hardness) | 79 | 175 | 178 | 169 |
|  | Syneresis suppressing effect (25° C.) | Δ | ○Δ | Δ | Δ |
|  | Foaming property | ○ | ○ | ○ | ○ |
|  | Productivity (80° C.) | Δ | Δ | ○ | ◎ |

TABLE 5

|  |  | Test example | | | |
|---|---|---|---|---|---|
|  |  | 5-1 | 5-2 | 5-3 | 5-4 |
| POE alkyl ether carboxylate | Laureth-6 carboxylic acid | 3.29 | 3.29 | 3.29 | 3.29 |
| Neutralizer | Triethanolamine | 0.85 | 0.85 | 0.85 | 0.85 |
| Anionic surfactant | Sodium cocoyl methyl taurate | 2.25 | 2.25 | 2.25 | 2.25 |
| Amphoteric surfactant | Cocamide propyl betaine | 4.47 | 4.47 | 4.47 | 4.47 |
| Gelling agent | Tamarind seed gum | 1.6 | 1.6 | 1.6 | 1.6 |
| Syneresis suppressing agent | Xanthan hydroxypropyl-trimonium chloride | 0.2 | 0.2 | 0.2 | 0.2 |
|  | Deacylated gellan gum | — | 0.05 | 0.1 | 0.2 |
| Moisturizer | Concentrated glycerin | 22 | 22 | 22 | 22 |
|  | Propanediol | 2 | 2 | 2 | 2 |
| Chelating agent | EDTA-3Na•2H2O | 0.2 | 0.2 | 0.2 | 0.2 |
| Solvent | Ion-exchanged water | to 100 | to 100 | to 100 | to 100 |
| Evaluation | Appearance (room temp.) | ○ | ○ | Δ | X |
|  | pH (1%) | 6.33 | 6.6 | 6.36 | 6.49 |
|  | Soap (gel hardness) | 81 | 100 | 121 | 141 |
|  | Syneresis suppressing effect (25° C.) | ○Δ | ○Δ | ○Δ | Δ |
|  | Foaming property | ○ | ○ | ○ | ○ |
|  | Productivity (80° C.) | Δ | ○ | ○ | ○ |

TABLE 6

|  |  | Test example | | | |
|---|---|---|---|---|---|
|  |  | 6-1 | 6-2 | 6-3 | 6-4 |
| POE alkyl ether carboxylate | Laureth-6 carboxylic acid | 3.29 | 3.29 | 3.29 | 3.29 |
| Neutralizer | Triethanolamine | 0.85 | 0.85 | 0.85 | 0.85 |
| Anionic surfactant | Sodium cocoyl methyl taurate | 2.25 | 2.25 | 2.25 | 2.25 |
| Amphoteric surfactant | Cocamide propyl betaine | 4.47 | 4.47 | 4.47 | 4.47 |
| Gelling agent | Tamarind seed gum | 1.6 | 1.6 | 1.6 | 1.6 |
| Syneresis suppressing agent | Xanthan hydroxypropyl-trimonium chloride | 0.3 | 0.3 | 0.3 | 0.3 |
|  | Deacylated gellan gum | — | 0.05 | 0.1 | 0.2 |
| Moisturizer | Concentrated glycerin | 22 | 22 | 22 | 22 |
|  | Propanediol | 2 | 2 | 2 | 2 |
| Chelating agent | EDTA-3Na•2H2O | 0.2 | 0.2 | 0.2 | 0.2 |
| Solvent | Ion-exchanged water | to 100 | to 100 | to 100 | to 100 |
| Evaluation | Appearance (room temp.) | ○ | ○ | Δ | X |
|  | pH (1%) | 6.43 | 6.4 | 7.09 | 6.27 |
|  | Soap (gel hardness) | 91 | 95 | 123 | 132 |
|  | Syneresis suppressing effect (25° C.) | ○Δ | ○ | ○ | ○ |
|  | Foaming property | ○ | ○ | ○ | ○ |
|  | Productivity (80° C.) | X | Δ | Δ | ○ |

When Test example 3-1 and Test example 3-5 of Table 3 are compared, Test example 3-5 of which the fatty acid soap was used as the cleansing component was insufficient in the foaming property; whereas, Test example 3-1 achieved a significant improvement in the foaming property by using polyoxyethylene alkyl ether carboxylate as the cleansing component.

However, in terms of suppressing syneresis of the gel formed by tamarind gum, it can be understood that it is insufficient with the deacylated gellan gum alone.

In the results shown in Tables 1 and 2, this point is in contrast to the point that the gellan gum alone exhibited the effect of suppressing syneresis of the gel formed by the tamarind gum, and an action of promoting syneresis is presumed to be provided by the cleansing component.

Whereas, referring to Tables 4 and 5, the effect of suppressing syneresis by cationized xanthan gum alone was confirmed from the results of Test examples 4-1, 5-1 and 6-1.

In addition, on the premise of the existence of the cationized xanthan gum, an enhanced effect of suppressing syneresis of the gellan gum was confirmed.

From the above results, by using polyoxyethylene alkyl ether carboxylate as the cleansing component of the cleansing agent gelled by tamarind gum, the foaming property can be remarkably increased, the pH can be suppressed to 7.5 or lower, and sensation to skin becomes mild.

Next, the present inventors studied on the counter ion of polyoxyethylene alkyl ether carboxylate.

The results are shown in the following Table 7.

TABLE 7

|  |  | Test example | | | | | | | |
|---|---|---|---|---|---|---|---|---|---|
|  |  | 7-1 | 7-2 | 7-3 | 7-4 | 7-5 | 7-6 | 7-7 | 7-8 |
| POE alkyl ether carboxylate | Laureth-6 carboxylic acid | 3.15 | 3.29 | 3.74 | 3.74 | 3.74 | 3.85 | 3.85 | 3.85 |
| Neutralizer | Triethanolamine | 0.85 | — | — | — | — | — | — | — |
|  | Tromethamine | — | 0.72 | — | — | — | — | — | — |
|  | KOH | — | — | 0.30 | 0.38 | 0.44 | — | — | — |
|  | NaOH | — | — | — | — | — | 0.22 | 0.28 | 0.32 |

TABLE 7-continued

|  |  | Test example | | | | | | | |
|---|---|---|---|---|---|---|---|---|---|
|  |  | 7-1 | 7-2 | 7-3 | 7-4 | 7-5 | 7-6 | 7-7 | 7-8 |
| Anionic surfactant | Sodium cocoyl methyl taurate | 2.25 | 2.25 | 2.25 | 2.25 | 2.25 | 2.25 | 2.25 | 2.25 |
| Amphoteric surfactant | Cocamide propyl betaine | 4.47 | 4.47 | 4.47 | 4.47 | 4.47 | 4.47 | 4.47 | 4.47 |
| Gelling agent | Tamarind seed gum | 1.6 | 1.6 | 1.6 | 1.6 | 1.6 | 1.6 | 1.6 | 1.6 |
| Syneresis suppressing agent | Xanthan hydroxypropyl-trimonium chloride | 0.2 | 0.2 | 0.2 | 0.2 | 0.2 | 0.2 | 0.2 | 0.2 |
|  | Deacylated gellan gum | 0.05 | 0.05 | 0.05 | 0.05 | 0.05 | 0.05 | 0.05 | 0.05 |
| Moisturizer | Concentrated glycerin | 22 | 22 | 22 | 22 | 22 | 22 | 22 | 22 |
|  | Propanediol | 2 | 2 | 2 | 2 | 2 | 2 | 2 | 2 |
| Chelating agent | EDTA-3Na•2H2O | 0.2 | 0.2 | 0.2 | 0.2 | 0.2 | 0.2 | 0.2 | 0.2 |
| Solvent | Ion-exchanged water | to 100 | to 100 | to 100 | to 100 | to 100 | to 100 | to 100 | to 100 |
| Evaluation | Neutralization rate | 80 | 80 | 63 | 80 | 92 | 63 | 80 | 92 |
|  | Appearance (room temp.) | ○ | ○ | ○ | ○ | ○ | ○ | ○ | ○ |
|  | pH (1%) | 6.66 | 6.66 | 5.85 | 6.33 | 6.89 | 5.72 | 6.29 | 6.28 |
|  | Soap (gel hardness) | 173 | 173 | 82 | 125 | 108 | 112 | 152 | 141 |
|  | Syneresis suppressing effect (25° C.) | ○△ | ○△ | ○△ | ○△ | ○△ | ○△ | ○△ | ○△ |
|  | Foaming property | ○ | ○ | ○ | ○ | ○ | ○ | ○ | ○ |
|  | Productivity (80° C.) | ○ | ○ | ○ | ○ | ○ | ○ | ○ | ○ |

As is obvious from Table 7, excellent effects similar to the above are exhibited when organic amines such as sodium hydroxide, potassium hydroxide, tromethamine (2-amino-2-hydroxymethyl-1,3-propanediol) are used as the neutralizer.

In addition, even if the addition amount of the neutralizer is less than the theoretical neutralization amount, it became obvious that the effect may be exhibited at about 60 to 90%.

In addition, the relationship between the neutralization rate of polyoxyethylene alkyl ether carboxylate and the measurement results of the pH of 1% aqueous solution, performed by the present inventors, is as follows.

|  | 60% neutralization | 90% neutralization | 100% neutralization |
|---|---|---|---|
| NaOH | about 5.7 | about 6.5 | about 7.8 |
| KOH | about 5.3 | about 6.3 | about 7.5 |

Accordingly, when the degree of neutralization is around 100%, it is presumed that the pH becomes higher and the color tone becomes unstable.

In addition, as shown in Table 8, it became obvious that the characteristics of the present invention as described above are seen commonly in polyoxyethylene alkyl ether carboxylate.

TABLE 8

|  |  | Test example | |
|---|---|---|---|
|  |  | 8-1 | 8-2 |
| POE alkyl ether carboxylate | Laureth-4 carboxylic acid | 3.12 | — |
|  | Laureth-5 carboxylic acid | — | 3.24 |
| Neutralizer | Tromethamine | 0.88 | 0.76 |
| Anionic surfactant | Sodium cocoyl methyl taurate | 2.25 | 2.25 |
| Amphoteric surfactant | Cocamide propyl betaine | 4.47 | 4.47 |
| Gelling agent | Tamarind seed gum | 1.6 | 1.6 |
| Syneresis suppressing agent | Xanthan hydroxypropyltrimonium chloride | 0.2 | 0.2 |
|  | Deacylated gellan gum | 0.05 | 0.05 |
| Moisturizer | Concentrated glycerin | 22 | 22 |
|  | Propanediol | 2 | 2 |
| Chelating agent | EDTA-3Na•2H2O | 0.2 | 0.2 |
| Solvent | Ion-exchanged water | to 100 | to 100 |
| Evaluation | Neutralization rate | 80 | 76 |
|  | Appearance (room temp.) | ○ | ○ |
|  | pH (1%) | 6.99 | 7.04 |
|  | Soap (gel hardness) | 108 | 148 |
|  | Syneresis suppressing effect (25° C.) | ○△ | ○△ |
|  | Foaming property | ○ | ○ |
|  | Productivity (80° C.) | ○ | ○ |

Next, the present inventors evaluated mildness to skin when polyoxyethylene alkyl ether carboxylate are used by the stinging irritation.

TABLE 9

|  |  | Test example | | |
|---|---|---|---|---|
|  |  | 9-1 | 9-2 | 9-3 |
| POE alkyl ether carboxylate | Laureth-6 carboxylic acid | 3.15 |  |  |
| Fatty acid | Lauric acid |  | 2.3 | 0.9 |
|  | Myristic acid |  |  | 1.5 |
| Neutralizer | Triethanolamine | 0.85 | 2.5 | 3.4 |
| Anionic surfactant | Sodium cocoyl methyl taurate | 2.25 | 2.25 | 2.25 |
| Amphoteric surfactant | Cocamide propyl betaine | 4.47 | 4.47 | 4.47 |
| Gelling agent | Tamarind seed gum | 1.6 | 1.6 | 1.6 |
| Syneresis suppressing agent | Xanthan hydroxypropyltrimonium chloride |  |  |  |
|  | Deacylated gellan gum |  | 0.05 |  |
| Moisturizer | Concentrated glycerin | 22 | 22 | 22 |
|  | Propanediol | 2 | 2 | 2 |
| Chelating agent | EDTA-3Na•2H2O | 0.2 | 0.2 | 0.2 |
| Solvent | Ion-exchanged water | to 100 | to 100 | to 100 |
| Evaluation | Appearance (room temp.) | ○ | ○ | ○ |
|  | High-temperature stability (browning) | ○ | △ | △ |
|  | pH (1%) | 7.19 | 7.98 | 8.03 |
|  | Soap (gel hardness) | 108 | 198 | 141 |
|  | Syneresis suppressing effect (25° C.) | ○△ | ○△ | ○△ |

TABLE 9-continued

| | Test example | | |
|---|---|---|---|
| | 9-1 | 9-2 | 9-3 |
| Foaming property | ◎ | ○ | Δ |
| Productivity (80° C.) | ○ | ○ | ○ |
| Stinging irritation | ○ | X | Δ |

As is obvious from Table 9, the pH was high when the fatty acid soap was used, and Test example 9-2 that used lauric acid as the main fatty acid tended to be high in the stinging irritation in particular.

However, when polyoxyethylene alkyl ether carboxylate was used (Test example 9-1), it can be seen that the pH was suppressed to 7.5 or lower, a sufficient foaming property could be achieved, and the stinging irritation was low. In addition, since the color-tone stability as the base is good, it will not change color when colored in various color tones.

In addition, as shown in Table 10, the gel cleansing agent had high functions including irritation and the foaming property when tromethamine was used as the neutralizer and sodium lauroyl methylaminopropionate was used as the other anionic surfactant.

TABLE 10

| | | Test example 10-1 |
|---|---|---|
| POE alkyl ether carboxylate | Laureth-6 carboxylic acid | 4.05 |
| Neutralizer | Tromethamine | 1.00 |
| Anionic surfactant | Sodium cocoyl methyl taurate | 2.25 |
| Amphoteric surfactant | Cocamide propyl betaine | 4.47 |
| Gelling agent | Tamarind seed gum | 1.6 |
| Syneresis suppressing agent | Xanthan hydroxypropyltrimonium chloride | 0.25 |
| | Deacylated gellan gum | 0.05 |
| Moisturizer | Concentrated glycerin | 25.0 |
| | Propanediol | 2.0 |
| Chelating agent | EDTA-3Na•2H2O | 0.2 |
| Solvent | Ion-exchanged water | to 100 |
| Evaluation | Appearance (room temp.) | ○ |
| | pH (1%) | 6.91 |
| | Soap (gel hardness) | 331 |
| | Syneresis suppressing effect (25° C.) | ○ |
| | Foaming property | ◎Δ |
| | Productivity (80° C.) | ○ |
| | Stinging irritation | ○ |

What is claimed is:

1. A gel cleansing agent comprising:
   2 to 11% by mass of polyoxyethylene alkyl ether carboxylate;
   0.5 to 3% by mass of xyloglucan; and
   0.2 to 3% by mass of a cationized xanthan gum,
   wherein the pH of 1% aqueous solution is 7.5 or lower, and wherein a neutralization rate of the polyoxyethylene alkyl ether carboxylate is 60 to 90%.

2. The gel cleansing agent of claim 1, wherein 0.01 to 0.5% by mass of a deacylated gellan gum is further comprised.

3. The gel cleansing agent of claim 1, wherein the polyoxyethylene alkyl ether carboxylate is POE (3-5) lauryl ether carboxylate.

4. The gel cleansing agent of claim 2, wherein the polyoxyethylene alkyl ether carboxylate is POE (3-5) lauryl ether carboxylate.

* * * * *